United States Patent [19]
Schutt

[11] 4,439,524
[45] Mar. 27, 1984

[54] STEREOSELECTIVE RESOLUTION OF PHENYLGLYCINE DERIVATIVES WITH ENZYME RESINS

[75] Inventor: Hermann Schutt, Wuppertal, Fed. Rep. of Germany

[73] Assignee: Bayer Aktiengesellschaft, Leverkusen, Fed. Rep. of Germany

[21] Appl. No.: 332,569

[22] Filed: Dec. 21, 1981

Related U.S. Application Data

[63] Continuation of Ser. No. 161,811, Jun. 23, 1980, abandoned.

[30] Foreign Application Priority Data

Jul. 7, 1979 [DE] Fed. Rep. of Germany ....... 2927535

[51] Int. Cl.$^3$ ............................................. C07B 20/00
[52] U.S. Cl. ..................................... 435/280; 435/813
[58] Field of Search ............... 435/280, 174, 176, 177, 435/178, 179, 180, 181, 813

[56] References Cited

U.S. PATENT DOCUMENTS 3,907,638  9/1975  Uzuki et al. ......................... 435/280
3,971,700  7/1976  Böesten ............................. 435/280
4,202,943  5/1980  Suhara et al. ....................... 435/280

Primary Examiner—Robert J. Warden
Attorney, Agent, or Firm—Sprung, Horn, Kramer & Woods

[57] ABSTRACT

The invention relates to a process for the stereo-selective resolution of DL-phenylglycine derivatives by hydrolyzing the ester or amide groups of N-acyl-L-phenylglycine esters or amides in N-acyl-DL-phenylglycine esters or amides by the action of enzymes, separating the N-acyl-D-phenylglycine esters or amides from the N-acyl-L-phenylglycines and then, if appropriate, subjecting the ester or amide groups of the D-enantiomers and the acyl groups to acid hydrolysis, characterized in that enzyme which are bonded to carriers are allowed to act on the N-acyl-DL-phenylglycine esters or amides in an inert two-phase mixture consisting of water-immiscible organic solvent and water.

10 Claims, No Drawings

STEREOSELECTIVE RESOLUTION OF PHENYLGLYCINE DERIVATIVES WITH ENZYME RESINS

This is a continuation of application Ser. No. 161,811 filed June 23, 1980 now abandoned.

The invention relates to a process for the stereoselective resolution of DL-phenylglycine derivatives by hydrolysing the ester or amide groups of N-acyl-L-phenylglycine esters or amides in N-acyl-DL-phenylglycine esters or amides by the action of enzymes, separating the N-acyl-D-phenylglycine esters or amides from the N-acyl-L-phenylglycines and then, if appropriate, subjecting the ester or amide groups of the D-enantiomers and the acyl groups to acid hydrolysis, characterised in that enzymes which are bonded to carriers are allowed to act on the N-acyl-DL-phenylglycine esters or amides in an inert two-phase mixture consisting of water-immiscible organic solvent and water.

D-Phenylglycine and D-4-hydroxyphenylglycine are used as starting substances for the preparation of semi-synthetic antibiotics of the penicillin series. L-Phenylglycine is a starting substance for L-asparagyl-L-phenylglycine methyl ester, which is used as a sweetener.

The method introduced industrially for resolving racemates of DL-phenylglycine and DL-4-hydroxyphenylglycine is fractional crystallisation of the salts of the two aminoacids with DL-camphorsulphonic acid (J. P. Greenstein and M. Winitz, Chemistry of Amino acids, volume 1 (1961) 658). Because of the high price of camphorsulphonic acid, this compound must be recovered as completely as possible, which can scarcely be realised on an industrial scale. There has thus been no lack of attempts to resolve racemates of derivatives of phenylglycine and of 4-hydroxyphenylglycine on a completely different basis to fractional crystallisation of diastereoisomeric compounds. The more recent processes attempt to utilise the high stereospecificity of certain enzymes. However, a number of disadvantages must be accepted in the processes hitherto disclosed.

In German Offenlegungsschrift No. 2,526,594, L-phenylglycine amide in DL-phenylglycine amide is hydrolysed to L-phenylglycine by an aminopeptidase suitable for this purpose, and is separated from unchanged D-phenylglycine amide. The enzyme used, leucine aminopeptidase (EC 3.4.1.1) is partly bonded to a carrier. This process can only be carried out in a very dilute medium, since the hydrolysis product L-phenylglycine, being sparingly soluble, would crystallise on the enzyme, and would thus halt the activities of the enzyme in a very short time. The result is that large volumes are formed and must be concentrated at the expense of consumption of energy to isolate the desired product. The same is true for the processes of German Offenlegungsschrift No. 2,621,076 and British Pat. No. 1,369,462, in which L-phenylglycine and L-4-hydroxyphenylglycine are formed from phenyl- or 4-hydroxyphenylhydantoins or from N-phenacetyl-DL-4-hydroxyphenylglycine.

Resolution of DL-2-acetamido-2-phenylacetic acid methyl ester, as a 3% strength aqueous suspension, by means of α-chymotrypsin without a carrier, into D-2-acetamido-2-phenylacetic acid methyl ester and L-2-acetamido-2-phenylacetic acid is furthermore known from Biochem. J. (1972), 126, 645–657, but only 60 and, respectively, 52.5% of theory of the products are obtained.

It has now been found, surprisingly, that the enzymatic resolution according to the invention can be carried out in a considerably higher concentration if the enzymatic hydrolysis is carried out in an inert two-phase water/with immiscible organic solvent mixtures on proteolytic enzymes which are bonded to carriers.

The compounds which are to be resolved correspond, in particular, to the formula (I)

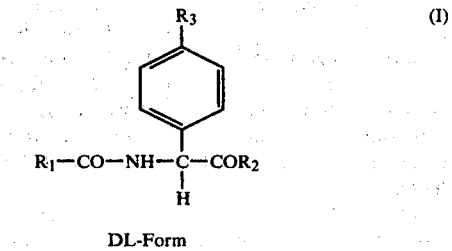

DL-Form wherein $R_1$ denotes hydrogen or the radical of an optionally substituted aliphatic or araliphatic monocarboxylic or dicarboxylic acid or of a naturally occurring or synthetic α-aminocarboxylic acid, $R_2$ denotes alkoxy, amino which is optionally mono-substituted or disubstituted by alkyl or the radical of a naturally occurring or synthetic α-aminoacid and $R_3$ denotes hydrogen, hydroxyl, alkoxy, aralkoxy, aryloxy, cycloalkoxy or acyloxy.

Optionally substituted aliphatic radicals $R_1$ are, above all, $C_1$–$C_9$-alkyl, $C_1$–$C_9$-carboxyalkyl, $C_2$–$C_9$-alkenyl or $C_1$–$C_9$-carboxyalkenyl groups which are optionally substituted by halogen, in particular fluorine or chlorine, preferably $C_1$–$C_4$-alkyl, $C_1$–$C_4$-carboxyalkyl, $C_2$–$C_4$-alkenyl or $C_2$–$C_4$-carboxyalkenyl groups which are optionally mono, di- or tri-substituted by flourine or chlorine; araliphatic radicals $R_1$ are, in particular, phenyl-$C_1$–$C_2$-alkyl groups or carboxyphenyl-$C_1$–$C_2$-alkyl groups, preferably the benzyl radical; the radicals $R_1$ and $R_2$ which are derived from α-aminoacids are, in particular, those from naturally occurring α-aminoacids; alkoxy groups $R_2$ are, in particular, $C_1$–$C_4$-alkoxy, preferably methoxy and ethoxy; amino groups which are optionally monosubstituted or disubstituted by alkyl (more particularly $C_1$–$C_4$-alkyl) are preferably amino and methylethyl-, dimethyl- and diethyl-amino; alkoxy defining $R_3$ is, in particular, $C_1$–$C_4$-alkoxy; aralkoxy defining $R_3$ is, in particular, benzyloxy; aryloxy defining $R_3$ is, in particular, phenyloxy; cycloalkoxy defining $R_3$ is, in particular, $C_5$- and $C_6$-cycloalkoxy; and acyloxy defining $R_3$ is, in particular, $C_1$–$C_4$-alkylcarbonyloxy which is optionally substituted by 1,2 or 3 fluorine or chlorine atoms.

Preferred compounds of the formula I are those in which $R_1$ denotes hydrogen, methyl, mono-, di- or tri-chloromethyl, trifluoromethyl or α-carboxy-$C_2$-$C_6$-alkyl, $R_2$ denotes methoxy or ethoxy and $R_3$ denotes hydrogen, hydroxyl, methoxy, ethoxy or acetoxy.

Possible inert solvents for the process are water-immiscible solvents, such as methylene chloride, chloroform, toluene, benzene, ethyl acetate, petroleum ether, methyl isobutyl ketone or isobutanol.

Possible enzymes are, in particular, proteolytic enzymes, especially serine proteases and sulfhydryl proteases, preferably subtilisin (EC 3.4.4.16), α-chymotrypsin (EC 3.4.4.5), papain (EC 3.4.4.10), ficin or bromelain, of which the first two have a serine radical in the active centre of the aminoacid chain, whilst the latter have cysteine as the active centre in the aminoacid chain. Subtilisin is preferred.

The enzyme bonded to a carrier can be re-used at least 75 times with only a slight loss in activity of about 0.1% per batch, whilst according to the process in the Biochem. J., soluble enzyme produces no conversion at all in the presence of water-immiscible solvents.

Proteolytic subtilisin which is isolated from *Bacillus subtilis* and *Bacillus licheniformis* and is added to washing agents to remove protein residues is particularly suitable. This industrial enzyme is primarily known by the tradenames Maxatase® (manufacturer: Gist-Brocades N.V., Delft/The Neterlands), Optimase® (manufacturer: Miles-Kali-Chemie, Hannover) and Alcalase® (manufacturer: Novo Industri AS, Copenhagen/Denmark).

The properties of the proteolytic enzymes, and in particular their biochemical actions, are described in the following literature: G. E. Perlmann and L. Lorand, Methods in Enzymology, 19 (1970), 199–215; P. Desnuelle, The Enzymes, 4 (1960), 93 and G. E. Perlmann and L. Lorand, Methods in Enzymology, 19 (1970), 226–244.

The proteolytic enzymes can be coupled to the polymeric carrier by a covalent bond via a lysine radical which is not essential for the catalysis. A further possibility is adsorption of the enzyme onto the pores of a charged carrier and subsequent crosslinking with glutarodialdehyde.

Possible enzyme carriers are polymeric, porous carriers, such as celluloses, for example DEAE- or CM-celluloses, modified polyacrylamide gels with amino groups or hydroxyl groups or various organic copolymers of acrylamide, methacrylates or methacrylamide and maleic anhydride, according to German Offenlegungsschriften Nos. 2,215,539 and 2,215,687.

A prior test for the adsorption of N-acyl-DL-phenylglycine esters or amides is a prerequisite for the suitability of an enzyme carrier for the process described. Suitable carriers should adsorb N-acyl-DL-phenylglycine esters or amides only to a very slight extent or not at all.

The various celluloses, cellulose derivatives, polyacrylamide gels containing amino groups or hydroxyl groups and the anhydride resins modified by amino groups or hydroxyl groups have proved particularly suitable carriers for the proteolytic enzymes. In general, all polymeric carriers which have amino groups or hydroxyl groups and which do not adsorb N-acyl-phenylglycine esters or amides can be used as the carriers.

The polymeric carrier is activated by methods which are known per se, using cyanuric chloride (British Patent No. 1,302,706, N. L. Smith and H. M. Lehnhoff, Anal. Biochem. 61 (1974), 92–415 and T. H. Finley, V. Troll, M. Levy, A. J. Johnson and L. T. Hodgins, Anal. Biochem. 87 (1978), 77–90) or various halogenopyrimidines according to German Offenlegungsschrift No. 2,619,521 and German Offenlegungsschrift No. 2,619,451.

The enzyme is coupled with the polymeric carrier by reaction under conditions which are optimum for the stability of the enzyme. The effectiveness of the coupling can be established by measuring the enzymatic activity on the polymer and in the wash water. When used in the batch process, the enzyme bonded to the carrier can easily be separated off from the reaction solution by sedimentation or filtration and can be employed several times. It is also possible to pack columns with the enzyme bonded to the carrier and to allow a substrate solution to flow through in the presence of a buffer system.

The N-acyl-phenylglycine esters and amides employed in the process according to the invention are obtained by acylating the corresponding aminoacid ester hydrochlorides or aminoacid amide hydrochlorides with stoichiometric amounts of an acid anhydride, such as acetic anhydride, and then separating off the N-acyl derivative from the aqueous phase using organic solvents, such as chloroform or methylene chloride.

Many of the substrates and products of enzyme reactions have only a limited solubility in water or buffer solutions. For economic reasons, however, substrate solutions which are as concentrated as possible should be used for the industrial application of reactions with enzymes bonded to carriers.

Numerous attempts have thus been made to achieve higher product concentrations, with enzymes, using water/solvent mixtures than can be achieved if an aqueous solution is used.

Observations show that dissolved, solvated enzymes can be partly or completely denatured by solvents, such as methanol, ethanol, acetone, acetonitrile, dioxane and dimethylformamide or dimethylsulphoxide, with partial or complete loss of the enzyme activity, and can be precipitated out of the solution.

Bonding the enzyme to a polymeric carrier prevents aggregation of the enzyme molecules, so that enzymes bonded to a carrier lose their activity to a considerably lesser extent than the free enzymes (K. Tamizawa and M. L. Bender, J. Biol. Chem. 249 (1974), 2130–2134). However, even in the case of enzymes bonded to a carrier, loss in the activity of the bonded enzyme as a result of the solvent is observed to a greater or lesser extent. Either an irreversible or a reversible inactivation of the enzyme is observed, the inactivation depending on the concentration of the solvent (H. Kaplan and K. J. Leidler, Canad. J. Chem. 45 (1967), 547–557, G. M. Umezurike, BioChem. J. 167 (1977), 831–833, T. N. Pattabiraman and W. B. Lawson, Biochem. J. 126 (1972), 645–657, G. Fink and H. Thoma, DECHEMA-Monographie 71, 295–314 and H. Wan and C. Horvath, Biophys. Biochem. Acta 410 (1973), 135–140).

The enzyme activity can also be altered, as a result of the influence of the solvent, by changing the pore size of the enzyme carrier.

However, the abovementioned completely water-miscible solvents have the further industrial disadvantage that they are difficult to separate off from water by distillation.

The use of water-immiscible solvents in reactions with enzymes bonded to carriers has hitherto been described in the literature in only one instance (A. M. Klibanov, G. P. Samokhin, K. Martinek and I. V. Berezin, Biotechnol. Bioeng. 19 (1977) 1351–1361). In the work cited, the synthesis of N-acetyl-L-tryptophane ethyl ester from N-acetyl-L-tryptophane and ethanol with chymotrypsin, covalently bonded to glass, in chloroform as the solvent is described. In order to be able to carry out the synthesis of the ester, which is unfavourable for energy reasons, the reaction must be carried out in the absence of water. This literature reference thus gives no indication at all of the process according to the invention.

The process according to the invention avoids all the disadvantages mentioned, and in addition protects the N-acyl-glycine esters from non-specific hydrolysis, so that the enzymatic resolution can also be carried out at relatively high pH values without loss of yield.

After covalent bonding to a polymeric carrier, the enzyme bonded to the carrier can be protected from the denaturing effect of solvents by subsequent intermolecular and intramolecular crosslinking with bivalent or polyvalent reagents, such as glutarodialdehyde or other reagents (F. Wold, Methods in Enzymology II, 617–640).

Enzymatic resolution of N-acyl-DL-phenylglycine esters is preferably effected at a temperature of 20°–40° C. in a pH range of 6–8, the pH value preferably being kept constant at pH 7.0 by adding a strong base. The substrate is added to the enzyme/carrier, which is suspended in water, as an approximately 10–20% strength organic solution, and the proportion of solvent can be at most 75–80% by volume, relative to the total volume. During the enzymatic reaction, the reaction medium is stirred intensively. The course of the enzymatic reaction and its end point can be determined by neutralisation of the H+ ions formed. Neutralisation can be effected by inorganic bases or by organic bases.

When the enzymatic reaction has ended and after the enzyme resin has settled, the organic phase is separated off and the aqueous reaction solution is extracted once more, in portions, with twice the volume of organic solvent. The extracts are combined. The enzyme resin is filtered off and the aqueous phase which remains is rendered acid, for example with sulphuric acid, and extracted with ethyl acetate. The optical purity of the resulting compounds is then examined.

Acid hydrolysis to give the D- or L-phenylglycines is then carried out by heating (60°–100° C.) the products in mineral acids, for example in 2 N hydrochloric acid, for several hours (2–48 hours). After cooling the solution, it is adjusted to pH 5–8 with sodium hydroxide solution or aqueous ammonia and cooled to +4° C. The phenylglycines which have crystallised out are filtered off, washed and dried.

It has already been disclosed that microbial and animal serine proteases, such as Carlsberg- and Novosubtilisins or chymotrypsin can resolve some N-acyl-DL-aminoacid esters (A. O. Barel and A. N. Glazer, J. Biol. Chem. 243 (1968), 1344–1348 and U.S. Pat. No. 3,963,573 and U.S. Pat. No. 3,878,043). However, these aminoacid esters differ considerably from the phenylglycine derivatives to be resolved according to the invention. According to Chemical Reviews 46 (1950), 69–153, in particular 119–122, similar results were not to be expected with acylated phenylglycine esters.

EXAMPLE 1

200 g of Cellulose Avicel (Merck) are suspended in a solution of 500 ml of water and 500 ml of dioxane, and 20 g of cyanuric chloride are added. The pH value is kept between pH 7.0 and 9.0 with 2 N NaOH. After stirring the mixture for 45 minutes, the activated cellulose is filtered off over a frit and suspended in 800 ml of water. 25 g of Maxatase (Gist-Brocades N. V., Delft/The Netherlands) are added and the mixture is stirred at room temperature and at pH 7–8 for 20 hours. Thereafter, the enzyme carrier is filtered off over a frit, washed in portions with distilled water and finally sucked dry.

600 g of moist subtilisin-cellulose are obtained. Activity: 284 ATEE (N-acetyl-L-tyrosine ethyl ester) units/g of enzyme carrier. Total activity: 170,250 ATEE units, corresponding to 27.2% of the activity employed.

EXAMPLE 2

100 g of DEAE-cellulose (DE-52-Cellulose, Messrs. Whatmann Ltd., Springfield/England) are activated with cyanuric chloride in a manner similar to that described above. 5 g of Maxatase or Alcalase which has been lyophilised after dialysis against water (659 Anson units/g, manufacturer: Novo AS, Copenhagen/Denmark) are covalently bonded thereto. 140 g of moist DE-52-Cellulose-subtilisin with 740 ATEE units/g of enzyme carrier are obtained after filtration.

The total yield of activity was 103,600 ATEE units, corresponding to 16.5% of the activity employed.

EXAMPLE 3

20 g of anhydride resin (80% by weight of tetraethylene glycol dimethacrylate, 10% by weight of methacrylic acid and 10% by weight of maleic anhydride) washed with acetone are suspended in 50 ml of water. 40 ml of 10% strength by weight hexamethylenediamine solution or ethanolamine solution are added at pH 7.0 and the suspension is kept overnight at a constant pH of 6.2 by titration. The amine resin is filtered off. Excess hexamethylenediamine is washed out with 1 M NaCl solution. The resin is then washed with desalinated water.

The anhydride resin carrying amino groups is suspended in 50 ml of water and 50 ml of dioxane and is activated with 2 g of cyanuric chloride at room temperature and at pH 5.0 for 1 hour. The resin is washed with dioxane and water and reacted with 2 g of Maxatase at room temperature and at pH 8.0 for 20 hours.

48.2 g of moist resin with an activity of 126 ATEE units/g of enzyme carrier are obtained.

The total yield of activity was 60,790 ATEE units, corresponding to 12.1% of the activity employed.

EXAMPLE 4

300 g of polyacrylonitrile resin which has been reacted with diethylenetriamine are activated as indicated above, in a weight ratio of carrier:cyanuric chloride of 10:1, and the activated resin is reacted with 30 g of Maxatase at 25° C. and at pH 8.0 for 16 hours.

288.5 g of moist enzyme resin are obtained.

The proteolytic activity on the carrier was 81.0 ATEE units/g of enzyme resin, namely a total of 23,383 ATEE units, corresponding to 3.1% of the total activity employed.

EXAMPLE 5

Preparation of soluble subtilisin bonded to a carrier 20 g of starch obtained by the method of Zulkowsky are dissolved in 500 ml of water, the solution is adjusted to pH 11.0 with 2 N NaOH, and 1.64 g of cyanogen bromide are added. The soluble polymeric carrier is activated, with the addition of 2 N NaOH, for 30 minutes at pH 11.0, measured on a pH meter. The pH value is then reduced to pH 7.0 with 2 N HCl, 2 g of dialysed and lyophilised Maxatase are added and the solution is stirred overnight at 14° C.

The proportion of Maxatase which has not been covalently bonded to the starch is removed via a DDS-600 ultrafilter.

Substilisin solution employed: 60,625 ATEE units.
Concentrate after ultrafiltration: 46,400 ATEE units=76.5% of the total activity.
Ultrafiltrate: 1,500 ATEE units=2.5% of the total activity.

EXAMPLE 6

Enzymatic resolution of N-formyl-DL-phenylglycine methyl ester and subsequent acid hydrolysis to give D-phenylglycine without a water-immiscible solvent.

30 g of N-formyl-DL-phenylglycine methyl ester are dissolved in 2 l of water, and 600 g of the subtilisin carrier prepared according to Example 1 are added, whilst stirring. The pH value of the solution is kept constant at pH 7.0 by adding 25% strength ammonia with a Methrom titration unit (pH value E 300 B, Impulsomat E 473 and Dosimat 412, Methrom, Herisau/Switzerland). After a reaction time of 15 hours at 37° C., the subtilisin carrier is filtered off over a frit and stored at 4° C. until used further. The resolution solution is concentrated to 500 ml on a rotary evaporator and the residue is extracted with methylene chloride in portions of 200 ml, 100 ml and once again 100 ml. The combined methylene chloride extracts are evaporated to dryness in a rotary evaporator.

The yield of N-formyl-D-phenylglycine methyl ester is 8.3 g (55.3% of theory, relative to 50% of the racemic derivative)

$$[\alpha]_{578\ nm}^{25°\ C.} = -200.0° \quad (c = 1 \text{ in methanol})$$

10 g of N-formyl-D-phenylglycine methyl ester are dissolved in 5% strength HCl to form a 10% strength solution and are hydrolysed at 85° C. for 24 hours. The hydrochloric acid is then stripped off in a rotary evaporator and the concentrate is adjusted to pH 4.5 with 15% strength sodium hydroxide solution. The resulting precipitate is filtered off, washed with distilled water and acetone and dried.

The yield of D-phenylglycine is 7.22 g (92.2% of theory, relative to N-formyl-D-phenylglycine methyl ester)

$$[\alpha]_{578\ nm}^{25°\ C.} = -158° \quad (c = 1 \text{ in 1 N HCl})$$

EXAMPLE 7

Enzymatic resolution of N-acetyl-DL-phenylglycine methyl ester in the presence of methyl isobutyl ketone and subsequent acid hydrolysis to give D-phenylglycine.

30 g of N-acetyl-DL-phenylglycine methyl ester are dissolved in an emulsion of 250 ml of water and 250 ml of methyl isobutyl ketone, and 288.5 g of the subtilisin resin prepared according to Example 4 are added. After stirring the mixture at 37° C. and at pH 7.0 for 7 hours, the stirrer is switched off and the organic phase is removed. The aqueous phase is then extracted twice more with 250 ml of methyl isobutyl ketone. The combined organic phases are evaporated to dryness in a rotary evaporator.

The yield of N-acetyl-D-phenylglycine methyl ester is 14.9 g (99.3% of theory).

$$[\alpha]_{578\ nm}^{25°\ C.} = -176.2° \quad (c = 1 \text{ in methanol})$$

14.9 g of N-acetyl-D-phenylglycine methyl ester are hydrolysed to D-phenylglycine, and the mixture is worked up, as described in Example 6.

The yield of D-phenylglycine is 7.9 g (82.4% of theory).

$$[\alpha]_{578\ nm}^{25°\ C.} = -164.2° \quad (c = 1 \text{ in 1 N HCl})$$

EXAMPLE 8

Enzymatic resolution of N-acetyl-DL-phenylglycine methyl ester in the presence of chloroform and subsequent acid hydrolysis to give D-phenylglycine.

30 g of N-acetyl-DL-phenylglycine methyl ester are dissolved in an emulsion of 800 ml of water and 200 ml of methylene chloride, and 140 g of the subtilisin carrier prepared according to Example 2 are added, whilst stirring. The enzymatic resolution and the working up are carried out as in Example 6.

The yield of N-acetyl-D-phenylglycine methyl ester is 12.75 g (85.0% of theory)

$$[\alpha]_{578\ nm}^{25°\ C.} = -172.7° \quad (c = 1 \text{ in methanol})$$

The hydrolysis of N-acetyl-D-phenylglycine methyl ester to give D-phenylglycine is carried out as described in Example 6.

EXAMPLE 9

Enzymatic resolution of N-acetyl-DL-4-acetoxyphenylglycine methyl ester and subsequent acid hydrolysis to give D- and L-4-hydroxy-phenylglycine.

30 g of N-acetyl-DL-4-acetoxyphenylglycine methyl ester are dissolved in a mixture of 1 l of water and 1 l of methyl isobutyl ketone and the ester is resolved with 100,000 ATEE units of DE-52-Cellulose-subtilisin at pH 7.0 and at 37° C. The pH value is kept constant at pH 7.0 with 25% strength ammonia for 8 hours. After switching off the stirrer, the organic pulse is removed and the aqueous phase is extracted twice more by stirring with 1 l of methyl isobutyl ketone each time. The combined organic phases are evaporated to dryness in a rotary evaporator.

The yield of N-acetyl-D-4-hydroxyphenylglycine methyl ester is 13.84 g (92.3% of theory)

$$[\alpha]_{578\ nm}^{25°\ C.} = -180.6° \quad (c = 1 \text{ in methanol})$$

The aqueous phase is adjusted to pH 1.5 with sulphuric acid and extracted three times with 1 l of ethyl acetate each time.

The yield of N-acetyl-L-4-hydroxyphenylglycine is 11.26 g (95.5% of theory)

$$[\alpha]_{578\ nm}^{25°\ C.} = +159.8° \quad (c = 1 \text{ in methanol})$$

2.5 g of N-acetyl-D-p-hydroxyphenylglycine methyl ester are hydrolysed, as a 10% strength solution in 5% strength HCl, at 85° C. for 48 hours. The solution is then cooled and the pH value is adjusted to 4–6 with 25% strength ammonia. The D-4-hydroxyphenylglycine which has precipitated is filtered off, washed on the filter with water and dried.

The yield of D-p-hydroxyphenylglycine is 1.69 g (90.2% of theory)

$$[\alpha]_{578\ nm}^{25°\ C.} = -158.2° \quad (c = 1 \text{ in } 1\ N\ HCl)$$

EXAMPLE 10

Enzymatic resolution of N-acetyl-DL-phenylglycine-n-butyl-ester in the presence of methyl isobutyl ketone and subsequent acid hydrolysis to give D-phenyl-glycine.

To 24,36 g of N-acetyl-DL-phenylglycine-n-butyl-ester dissolved after chemical synthesis in 200 ml methyl isobutyl ketone 800 ml of water and 400 g subtilisin resin prepared according to Example 2 are added. After stirring the mixture for 6 hours at pH 8,0 and at 37° C., the organic phase is removed and evaporated to dryness in a rotary evaporator.

The yield of N-acetyl-D-phenylglycine-n-butyl-ester is 24,03 g (98,6% of theory)

$$[\alpha]_{578\ nm}^{25°\ C.} = -127,9° \quad (c = 1 \text{ in methynol})$$

20 g of N-acetyl-D-phenylglycine-n-butyl-ester are hydrolyzed to D-phenylglycine and the mixture is worked up as described in Example 6.

The yield of D-phenylglycine is 9.98 g (87,6% of theory)

$$[\alpha]_{578\ nm}^{25°\ C.} = -165,9° \quad (c = 7 \text{ in } 1\ N\ HCl)$$

EXAMPLE 11

Asymmetric resolution of N-acetyl-DL-phenylglycine methyl ester with soluble subtilisin bonded to a carrier 30 g of N-acetyl-DL-phenylglycine methyl ester are dissolved in 500 ml of methyl isobutyl ketone at room temperature. The organic phase is added to 970 ml of the soluble subtilisin which is bonded to a carrier and prepared according to Example 9 and the emulsion is stirred at 37° C. and at pH 7.0 for 15 hours. The organic phase is separated off and evaporated to dryness.

The yield of N-acetyl-D-phenylglycine methyl ester is 13.6 g (90.9% of theory)

$$[\alpha]_{578\ nm}^{25°\ C.} = -178.0° \quad (c = 1 \text{ in methanol})$$

The soluble, polymeric subtilisin can be recovered from the aqueous phase by ultrafiltration over a DDS-600 ultrafilter, or the aqueous phase can be employed several times with the organic phase for racemate resolution, without isolating the polymeric enzyme.

What is claimed is:

1. In a process for the stereoselective resolution of DL-phenylglycine derivatives by hydrolysing the ester or amide grooups of N-acyl-L-phenylglycine esters or amides in N-acyl-DL-phenylglycine esters or amides by the action of enzymes, separating the N-acyl-D-phenylglycine esters or amides from the N-acyl-L-phenylglycines and then, if desired, subjecting the esters or amide groups of the D-enantiomers and the acyl groups to acid hydrolysis, the improvement which comprises allowing enzymes selected from the group consisting of a sevine or sulfhydryl protease which are bonded to carriers to act on the N-acyl-DL-phenylglycine esters or amides in an inert two-phase solvent mixture consisting of water-immiscible organic solvent and water in a pH range of 6–8.

2. Process according to claim 1, characterised in that a compound of the formula

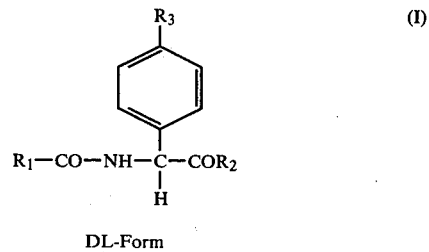

DL-Form wherein
$R_1$ denotes hydrogen or the radical of an optionally substituted aliphatic or araliphatic monocarboxylic or dicarboxylic acid or of a naturally occurring or synthetic α-aminocarboxylic acid,
$R_2$ denotes alkoxy, amino which is optionally mono-substituted or disubstituted by alkyl or the radical of a naturally occurring or synthetic α-aminoacid and
$R_3$ denotes hydrogen, hydroxyl, alkoxy, aralkoxy, aryloxy, cycloalkoxy or acyloxy,
is used as the substrate.

3. Process according to claim 2,
wherein
$R_1$ denotes hydrogen, methyl, mono-, di- or trichloromethyl, trifluoromethyl or α-carboxy-$C_2$-$C_6$-alkyl,
$R_2$ denotes methoxy or ethoxy and
$R_3$ denotes hydrogen, hydroxyl, methoxy, ethoxy or acetoxy.

4. Process according to claim 1, characterised in that methylene chloride, chloroform, toluene, benzene, ethyl acetate, petroleum ether, methyl isobutyl ketone or isobutanol is employed as the water-immiscible solvent.

5. Process according to claim 1, characterised in that celluloses, cellulose derivatives, polyacrylamide gels containing amino groups or hydroxyl groups or anhydride resins modified by amino groups or hydroxyl groups are employed as the carrier for the enzyme.

6. Process according to claim 1, characterized in that subtilisin is employed as the enzyme.

7. Process according to claim 1, wherein the water-immiscible solvent is methyl isobutyl ketone.

8. Process according to claim 1, wherein the water-immiscible solvent is chloroform.

9. Process according to claim 1 wherein the enzyme employed is selected from the group consisting of subtilisin, α-chymotrypsin, papain, ficin and bromelain.

10. Process according to claim 9 wherein the enzyme is α-chymotrypsin.

* * * * *

UNITED STATES PATENT AND TRADEMARK OFFICE
CERTIFICATE OF CORRECTION

PATENT NO. : 4,439,524

DATED : March 27, 1984

INVENTOR(S) : Hermann Schutt

It is certified that error appears in the above-identified patent and that said Letters Patent is hereby corrected as shown below:

| | |
|---|---|
| Abstract, line 10 | Delete "enzyme" and substitute --enzymes-- |
| Col. 3, line 16 | Delete "Neterlands" and substitute --Netherlands-- |
| Col. 6, line 65 | Delete "14°C" and substitute --+4°C-- |
| Col. 8, line 44 | Delete "pulse" and substitute --phase-- |
| Col. 9, line 62 | Delete "grooups" and substitute --groups-- |
| Col. 10, line 5 | Delete "sevine" and substitute --serine-- |

Signed and Sealed this

Fourth Day of December 1984

[SEAL]

Attest:

GERALD J. MOSSINGHOFF

*Attesting Officer*    *Commissioner of Patents and Trademarks*